(12) United States Patent
Burnett (10) Patent No.: US 10,413,225 B1
(45) Date of Patent: Sep. 17, 2019

(54) PULSE OXIMETER SENSOR ASSEMBLY AND METHODS OF USING SAME

(71) Applicant: Government of the United States, as represented by the Secretary of the Air Force, Wright-Patterson AFB, OH (US)

(72) Inventor: Gregory M. Burnett, Dayton, OH (US)

(73) Assignee: Government of the United States as represented by the Secretary of the Air Force, Wright-Patterson AFB ( * ) Notice: Subject to any disclaimer, the term of this patent is extended or adjusted under 35 U.S.C. 154(b) by 276 days.

(21) Appl. No.: 14/755,020

(22) Filed: Jun. 30, 2015

(51) Int. Cl.
  *A61B 5/00* (2006.01)
  *A61B 5/1455* (2006.01)
  *A61B 5/024* (2006.01)

(52) U.S. Cl.
  CPC ........ *A61B 5/14552* (2013.01); *A61B 5/0022* (2013.01); *A61B 5/02416* (2013.01); *A61B 5/6814* (2013.01); *A61B 5/7282* (2013.01); *A61B 5/742* (2013.01); *A61B 5/7405* (2013.01); *A61B 5/7455* (2013.01); *A61B 2560/0242* (2013.01)

(58) Field of Classification Search
  CPC .............. A61B 5/02444; A61B 5/1455; A61B 5/14551
  See application file for complete search history.

(56) References Cited

U.S. PATENT DOCUMENTS

| 7,988,511 | B2 | 8/2011 | Bissell, IV et al. |
| 8,172,459 | B2 | 5/2012 | Abreu |
| 8,688,187 | B2 | 4/2014 | DelloStritto et al. |
| 8,920,332 | B2 | 12/2014 | Hong et al. |
| 2002/0041231 | A1* | 4/2002 | Drinkard .............. G08B 13/193 340/541 |
| 2010/0081892 | A1* | 4/2010 | Sethi ..................... A61B 5/0205 600/301 |
| 2011/0148642 | A1* | 6/2011 | Cutler .................. G08B 21/088 340/573.6 |
| 2012/0029367 | A1* | 2/2012 | Hobeika ............ A61B 5/02416 600/500 |
| 2012/0065486 | A1 | 3/2012 | Imran |
| 2012/0095306 | A1 | 4/2012 | Egozi |
| 2013/0104288 | A1* | 5/2013 | Schlottau ............... A41D 1/002 2/209.13 |

(Continued)

OTHER PUBLICATIONS http://www.nonin.com/Sensors; downloaded on Jun. 29, 2015; 2 pages.

*Primary Examiner* — Christian Jang (74) *Attorney, Agent, or Firm* — AFMCLO/JAZ; Chastity D. S. Whitaker (57) ABSTRACT

A pulse oximeter sensor assembly and a method for monitoring and assessing a physical state of a subject with the assembly are provided. The assembly includes a pulse oximeter sensor, an indicator device, a processor coupled to the pulse oximeter sensor and the indicator device, a base layer configured to conform to a temporal region of the subject's head, and a mounting assembly configured to enable securing of the pulse oximeter sensor assembly in the temporal region of the subject's head. By positioning the assembly in the temporal region of the subject's head, the assembly can utilized data taken from the temporal artery and provide an external indication as to the physical status of the subject.

11 Claims, 5 Drawing Sheets

(56) References Cited

U.S. PATENT DOCUMENTS

| | | | | |
|---|---|---|---|---|
| 2013/0317753 A1* | 11/2013 | Kamen | ............... | G06F 19/3412 702/19 |
| 2014/0081098 A1* | 3/2014 | Cohrs | ................ | A61B 5/02444 600/324 |
| 2015/0031970 A1* | 1/2015 | Lain | ................... | A61B 5/14551 600/323 |

* cited by examiner

PULSE OXIMETER SENSOR ASSEMBLY AND METHODS OF USING SAME

RIGHTS OF THE GOVERNMENT

The invention described herein may be manufactured and used by or for the Government of the United States for all governmental purposes without the payment of any royalty.

FIELD OF THE INVENTION

The present invention generally relates to the field of diagnostic instruments including wearable sensors, and more particularly to a pulse oximeter sensor assembly adapted to be positioned in a temporal region on a subject's head and methods of using same.

BACKGROUND

Pulse oximeter (or pulse-ox) assemblies include sensors that are configured to measure heart beat rate and/or the oxygen saturation of the blood, and are of particular importance in emergency medical situations as well as the monitoring of patients with respiratory or cardiac problems. Generally, pulse oximeters operate by directing light, such as in the red and/or infrared wavelength range, from one or more light emitting diodes (LEDs) toward the skin and blood vessels. In operation, the pulse-ox assembly emits light from the LED(s), and a photodiode collects the light reflected from the subject's body (reflectance pulse oximetry) or transmitted through the subject's body part (transmissive pulse oximetry). Light in the red wavelength range is absorbed at a different rate than the infrared light. Accordingly, the ratio of oxyhemoglobin and deoxyhemoglobin can be calculated from the respective amounts of reflected or transmitted light.

To reduce potential interference, prior art pulse-ox sensors are generally configured to be worn on intrusive portions of the body such as wrists, fingers, or ear lobes. The measured heart rate and blood oxygen saturation of the subject is then reported on a local digital display or transmitted using wireless communication connections (e.g. bluetooth) to a remote display or system.

Adoption and implementation of typical pulse oximetry technology is practical in hospitals or home settings where the subjects are generally sedentary, however under exercise environments, such swimming or diving settings, it may be problematic. For example, blood flow is increased to the muscles that are being worked during exercise, thereby reducing blood flow to the extremities, such as hands, making them cooler. In turn, blood vessels in the extremities may open wider, which may then lead to blood pooling. Accordingly, monitoring SPO2 in the extremities of an exercising subject may lead to inaccurate vital signs readings. And wearing sensors on fingers or wrists is cumbersome during exercise (e.g., swimming) and may become detached through vigorous activities. Moreover, self-monitoring is not practical for those engaged in other cognitive and physical activities.

Therefore, a need exist for new pulse-ox sensor assemblies that overcome one or more of the problems of the prior art.

SUMMARY

The present invention overcomes one or more of the foregoing problems and other shortcomings, drawbacks, and challenges of typical pulse oximeters. While the invention will be described in connection with certain embodiments, it will be understood that the invention is not limited to these embodiments. To the contrary, this invention includes all alternatives, modifications, and equivalents as may be included within the spirit and scope of the present invention.

In accordance with an embodiment of the present invention, a pulse oximeter (pulse-ox) sensor assembly is provided. The assembly comprises a pulse oximeter sensor configured to evaluate conditions in a temporal region of a subject and generate a pulse-ox output signal in response thereto; an indicator device; a processor coupled to the pulse oximeter sensor and the indicator device; a base layer configured to conform to the temporal region of the subject's head, and which includes a first surface adapted to contact and face the subject's skin, and a second surface adapted to face away from the subject's skin; and a mounting assembly configured to secure the pulse oximeter sensor assembly in the temporal region of the subject's head and maintain the pulse oximeter sensor positioned overlying a portion of a temporal artery of the subject. The processor includes control logic configured to 1) receive the pulse-ox output signal from the pulse oximeter sensor; 2) determine the subject's heart beat rate, blood oxygen saturation level, or both; 3) generate an output signal that is based on the subject's heart beat rate, blood oxygen saturation level, or both; and 4) transmit the output signal to the indicator device.

In accordance with another embodiment, a method for monitoring and assessing a physical state of a subject is provided. The method includes positioning the pulse-ox sensor assembly over the temporal region of the subject's head, wherein the pulse-ox sensor is positioned over a portion of the temporal artery; obtaining the pulse-ox output signal from the pulse oximeter sensor, wherein the pulse-ox output signal contains data relating to the subject's heart beat rate, blood oxygen saturation level, or both; comparing the subject's heart beat rate to a predetermined threshold heart beat rate, and/or comparing the subject's blood oxygen saturation level to a predetermined threshold blood oxygen saturation level; and generating an external signal that is indicative of whether the predetermined threshold heart beat rate and/or the predetermined threshold blood oxygen saturation level have been crossed over.

Additional objects, advantages, and novel features of the invention will be set forth in part in the description which follows, and in part will become apparent to those skilled in the art upon examination of the following or may be learned by practice of the invention. The objects and advantages of the invention may be realized and attained by means of the instrumentalities and combinations particularly pointed out in the appended claims.

BRIEF DESCRIPTION OF THE DRAWINGS

The accompanying drawing, which are incorporated in and constitute a part of this specification, illustrate embodiments of the invention and, together with a general description of the invention given above, and the detailed description given below, serve to explain the invention. It will be appreciated that for purposes of clarity and where deemed appropriate, reference numerals have been repeated in the figures to indicate corresponding features.

It should be understood that the appended drawings are not necessarily to scale, presenting a somewhat simplified representation of various features illustrative of the basic principles of the invention. The specific design features of the sequence of operations as disclosed herein, including, for example, specific dimensions, orientations, locations, shapes, and colors of various illustrated components, will be determined in part by the particular intended application and use environment. Certain features of the illustrated embodiments have been enlarged or distorted relative to others to facilitate visualization and clear understanding.

DETAILED DESCRIPTION OF EMBODIMENTS OF THE INVENTION

Military personal who enter into specialized career fields such as combat control, pararescue, and other special operation forces and special tactics positions are required to master aquatic skills. Although at times, aquatic conditioning may prove to be too strenuous for swimmers and potentially necessitate medical intervention. The assemblies and methods described herein provide alerts when vital signs (e.g., SPO2 and/or HR) deteriorate to a predetermined threshold value prior to the need for medical intervention and thereby enable standoff monitoring of a swimmer's vitals. Embodiments described herein provide an assembly and method for sub-surface (underwater) and/or aquatic (within) monitoring of various vital signs (e.g., heart rate (HR), blood oxygen saturation (SPO2), etc.) of a subject in an aquatic environment and providing the subject and/or others with external overt notifications. However, it should be further appreciated that the assemblies describe herein may also be utilized in non-aqueous environments.

Thus, in accordance with embodiments of the present invention, a pulse oximeter (pulse-ox) sensor assembly is provided that includes 1) a pulse-ox sensor, 2) an indicator device, 3) a processor, 4) a base layer, and 5) a mounting assembly. The pulse-ox sensor is configured to facilitate measuring a subject's heart beat rate, blood oxygen saturation level, or both. The indicator device provides a discernible signal to the subject or others, (e.g., communication via optical modulation to an underwater and/or above water receiver). The processor, which is coupled to the pulse-ox sensor and the indicator device, includes control logic configured to receive an output signal from the pulse-ox sensor, determine the subject's heart beat rate, blood oxygen saturation level, or both, and generate an output signal for the indicator device that is based on the subject's heart beat rate, blood oxygen saturation level, or both. The base layer is configured to conform to a temporal region of the subject's head and includes one surface adapted to face and contact the subject's skin, and a second surface adapted to face away from the subject's skin. The mounting assembly is configured to enable securing and/or maintaining the pulse-ox sensor assembly over the temporal region of the subject's head, which, relative to more distal extremities (e.g., fingers or wrists), is less prone to blood pooling. The pulse-ox sensor assembly may also include a power supply, which can include a chamber that is adapted to hold and maintain a battery in electrical communication with the pulse-ox sensor, the processor, and the indicator device.

With more detail and specificity, the foregoing exemplary components are further described with reference to FIGS. 1-4, which provide complementary views of an exemplary embodiment.

Pulse Oximeter Sensor

Figure 1:
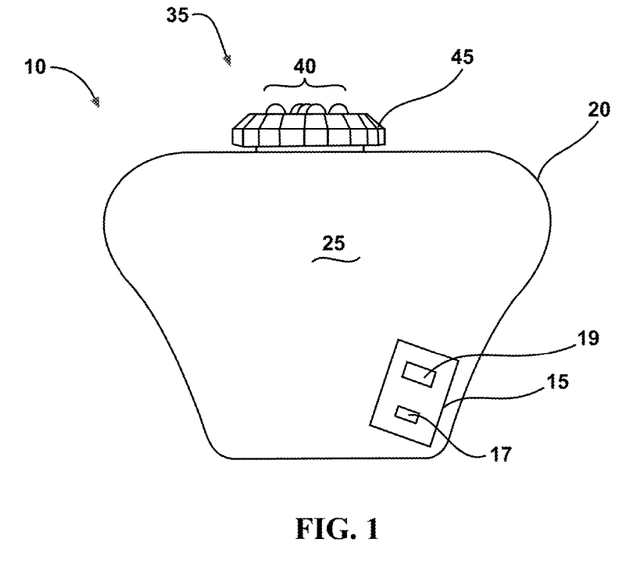
FIG. 1 is a view of a subject-facing side of a pulse-ox sensor assembly, in accordance with an embodiment of the present invention.

Referring to FIG. 1, an exemplary pulse-ox sensor assembly 10 is provided with a pulse-ox sensor 15 disposed in a base layer 20. The pulse-ox sensor 15 includes at least one light emitting diode (LED) 17 configured to emit light such as in the red and/or infrared range and at least one photodetector 19 configured to receive the light emitted by the at least one LED 17 and reflected by a subject's body (not shown) when in use and disposed proximate the body. The LED 17 and photodetector 19 cooperate to evaluate conditions observed in a region of the subject's skin, e.g., the temporal region. One exemplary pulse-ox sensor 15 is an 8000R Reflectance Sensor available from Nonin Medical, Inc. According to the depicted embodiment in FIG. 1, the pulse-ox sensor 15 is adapted to fit within an opening formed in the base layer 20. According to another embodiment, the pulse-ox sensor 15 may be embedded in the base layer 20. In either arrangement, it is advantageous that the pulse-ox sensor 15 does not protrude too far above a subject-facing side 25 of the assembly 10 as to cause undue discomfort to the subject. In one embodiment, the subject-facing surface 25 of base layer 20 and the pulse-ox sensor 15 are substantially uniplanar. In yet another embodiment, the pulse-ox sensor 15 is within about 0.5 mm, about 1 mm, about 2 mm, about 3 mm, or about 4 mm of the subject-facing surface 25 of the base layer 20. In yet another embodiment, base layer 20, could have a slidable adjustment for the pulse-ox sensor 15 to accommodate custom fitting to the subject's temporal artery.

Processor

Figure 3:
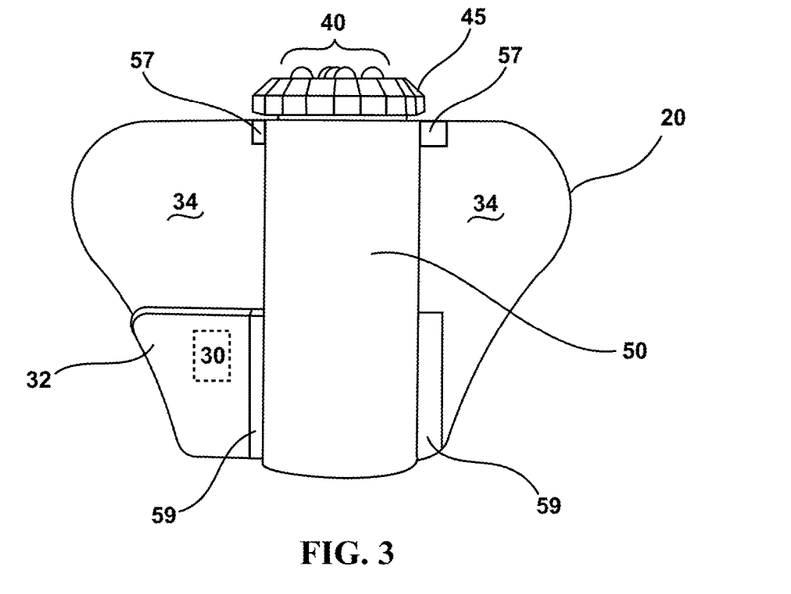
FIG. 3 is a view of an outward-facing side of the pulse-ox sensor assembly shown in FIG. 1, in accordance with an embodiment of the present invention.
Figure 4:
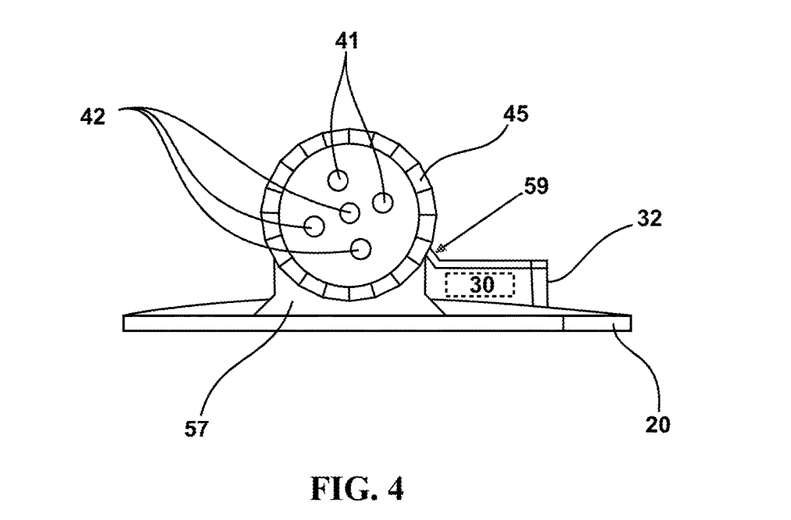
FIG. 4 is top view of the pulse-ox sensor assembly shown in FIG. 1, in accordance with an embodiment of the present invention.

The pulse-ox sensor 15 is configured to electrically communicate with a processor 30, which may be contained in and protected by an electronics compartment 32. To permit continual use of the assembly 10 in a water environment, the electronic compartment 32 may provide a water-proof or water-resistant containment of the processor 30, as well as any other water-sensitive electronic components. The electronics compartment 32 is preferably made of waterproof material. In other embodiments of the invention, the electronics compartment 32 may be made of materials that are merely water resistant. As used herein, "water resistant" refers to material that is capable, at least, of resisting or impeding the passage of liquid water by mass flow, capillary or wicking action. Thus, water resistant material may not prevent all passage of liquid water under pressure. "Water tight" refers to connections between components that are at least water resistant. As used herein, "waterproof" refers to the capability of withstanding immersion in water. Such immersion could be as little as splashing or dropping the assembly on or in water, or by submersion to a depth of about 10 cm, about 1 m, about 10 m, about 50 m, or about 100 m, in sea or freshwater. Waterproof material can range from gas proof to gas permeable, including such breathable fabrics and fabric coatings such as Gore-Tex®. The electronics compartment 32 may in certain applications be constructed to be not only waterproof, but also gas-proof, such that gases cannot escape or enter the sealed electronics compartment 32. The assembly 10 may therefore be particularly useful to swimmers and divers. As shown in FIGS. 3 and 4, the electronics compartment may be positioned on an outward-facing surface 34 of the base layer 20.

The processor 30, which is coupled to the pulse-ox sensor 15 and an indicator device 35, may include control logic configured to a) receive an output signal from the pulse-ox sensor 15, b) determine the subject's heart beat rate, blood oxygen saturation level, or both, and c) generate an output signal for the indicator device 35 that is based on the subject's heart beat rate, blood oxygen saturation level, or both. The output signal may include data that provides numerical values of the measured vital signs, or simply designate if a threshold value for a vital sign has been crossed. The threshold value for a specific vital sign may be a value set within control logic of the processor 30 or it may be a value that is self-adjusting based on certain trials, exercises, routines, etc. For example, the threshold value may be based on one or more exercise routines (i.e., empirically derived), which can then be stored in memory, thereby permitting personalization of the threshold values for a given subject. The threshold value may also be based on multiple previous uses, which then updates the threshold value based on averaging the current use with the multiple previous uses.

In addition to the processor 30, other electronic components that may be present in the electronic compartment 32 include, but are not limited to, a network interface, a data storage device, and/or electrical connections therebetween. When present, the network interface can be configured to communicate data by a protocol such as universal serial bus (USB), Wi-Fi, Bluetooth, IrDA, radio frequency, IEEE 802.11, IEEE 802.15, Zigbee, and/or free space optical (FSO) communication. When present, the data storage device can include local, network-accessible, removable/nonremovable, volatile/nonvolatile, and/or transitory/non-transitory memory, such as RAM, ROM, firmware and/or flash and can be further configured to store program instructions that, when implemented by the processor, are configured to communicate with the pulse-ox sensor 15 and specifically to operate the LED(s) 17 and photodetector(s) 19 so as to receive data/information based on light reflected from the patient's body when the pulse-ox is in use. One or more of the processor 30, network interface, power supply, and data storage device can be configured to mount on a printed circuit board, each or all of which may be individually or collectively covered by waterproof or water-resistant materials. In some embodiments of the disclosed invention, substantially all electronic components may be encapsulated in an epoxy, urethane, silicone, resin, or the like, to hermitically seal against contamination ingress.

Indicator Device

In an embodiment, the indicator device 35 may provide information relating to the absolute values of the measured vital signs. In another embodiment, the indicator device 35 may provide information as to the measured vital signs relative to the threshold value. In yet another embodiment, the indicator device 35 may provide information for both the absolute measurement and its relation to the threshold value. Accordingly, the indicator device 35 may provide the information visually, audibly, physical stimulation, or a combination thereof, and may transmit the information for standoff monitoring. For example, the indicator device may include a light source, such as constant or flashing lights, one or more LEDs, or LCD displayed messages; a noise source, such as speakers that provide an audible tone; or a haptic device in contact with the subject that emits vibrating pulses; and/or a radiation transmitter. By way of further example, the indicator device 35 may be adapted to provide audible beeps through bone conductive transducers and tactile vibration along with visual alerts. Further, standoff notification alternatives can use a variety of frequencies to be picked up underwater and rebroadcasted through other protocols in pool settings. Moreover, each pulse-ox sensor assembly 10 may have a unique frequency output, or a common frequency with uniquely coded device identifiers, allowing for specific notification for individual swimmers.

In accordance with the embodiment shown in FIGS. 1-4, the indicator device 35 may provide a visual notification through an LED array 40, which may be a colored, multi-spectral LED cluster and may alert other subjects or standoff observers when the subject requires medical intervention, crosses a vital sign threshold, or is within a safe vital sign range. For example, the LED array 40 may comprise at least a first color indicator LED 41 and a second color indicator LED 42. Additionally, the LED array, the output of which may be modulated, may provide a positive identification for swimmers above surface and sub-surface. Furthermore, the modulation of the LED array 40 may provide the means for free space optical (FSO) communication to off-board receivers transmitting the swimmers state. In accordance with an embodiment, the LED array 40 may be conveniently housed in a cap 45 of battery chamber 50.

Battery Chamber

Figure 2:
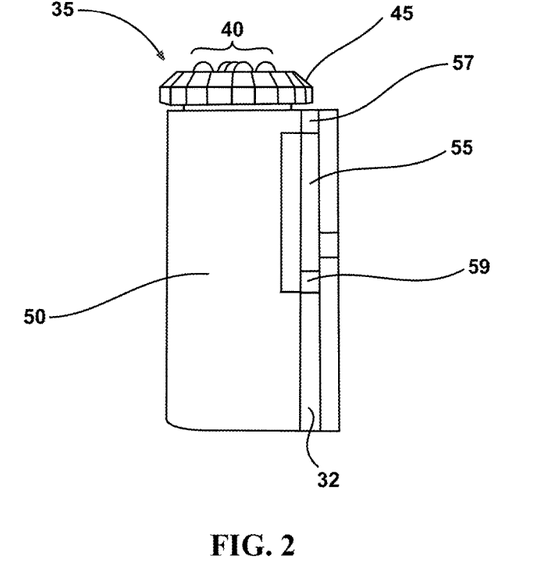
FIG. 2 is a side view of the pulse-ox sensor assembly shown in FIG. 1, in accordance with an embodiment of the present invention.

It will be readily apparent that any convenient portable power source (i.e., a battery) can be adapted to supply the electrical requirements for the pulse-ox sensor assembly 10. In an embodiment, the battery is contained within a battery chamber 50. To enable easy battery replacement, the battery chamber cap 45 and the battery chamber 50 may form a resealable, watertight connection (e.g., a screw cap with rubber O-ring). It should be appreciated that the form of the battery chamber 50 may modified or customized to accommodate virtually any battery shape. For example, as shown in FIG. 2, the battery chamber 50 is formed to accommodate a cylindrical battery, such as a typical AA or AAA battery.

Figure 5A:
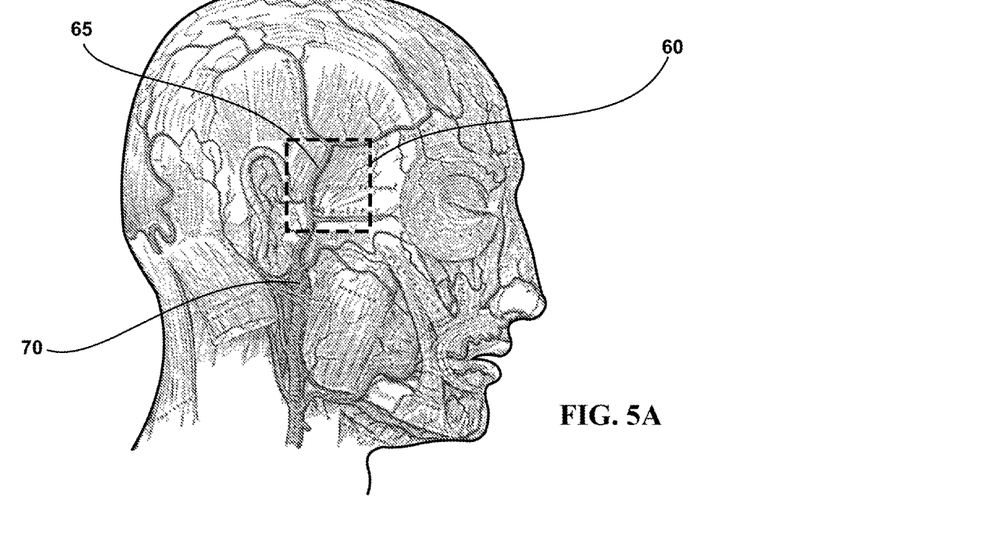
FIG. 5A is a schematic showing the location of a temporal artery in a human subject.
Figure 5B:
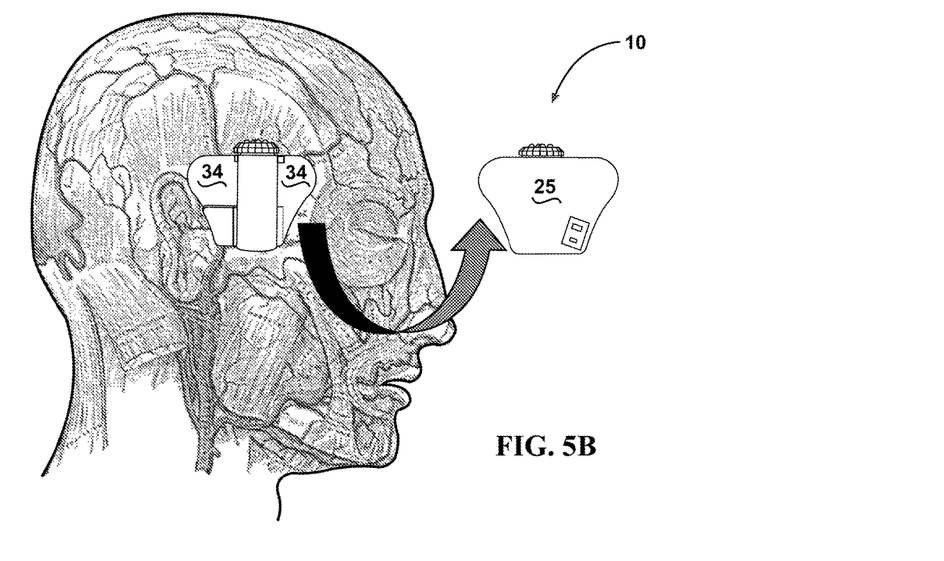
FIG. 5B is a schematic showing placement of the pulse-ox sensor assembly shown in FIG. 1 onto a subject's temporal region overlaying the temporal artery, in accordance with an embodiment of the present invention.
Figure 6:
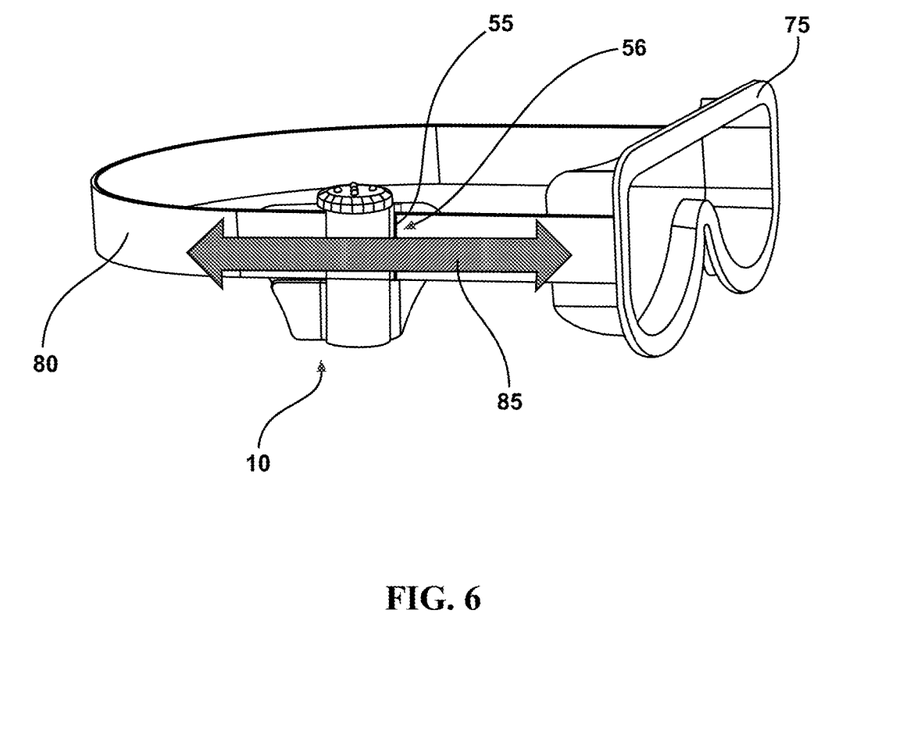
FIG. 6 is a perspective view of a pulse-ox sensor assembly, in accordance with another embodiment of the present invention.
Figure 7:
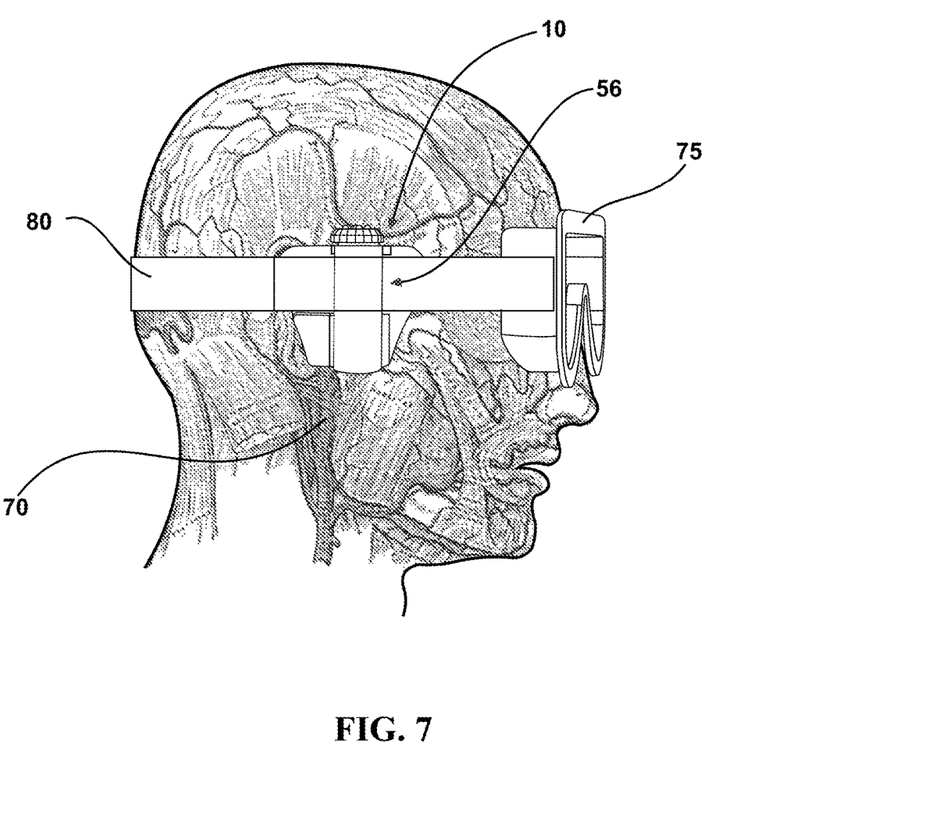
FIG. 7 is a schematic showing placement of the pulse-ox sensor assembly shown in FIG. 6 onto a subject's temporal region, in accordance with another embodiment of the present invention.

In accordance with another embodiment, the battery chamber 50 may be connected or joined to the base layer 20 in a manner that provides an aperture 55 between the two, which may serve as a mounting assembly 56 to accommodate a retaining strap (e.g., a goggle strap 80, as shown in FIGS. 6 and 7). For example, the battery chamber 50 may be connected to the base layer 20 by an upper support 57 and a lower support 59, which thereby forms the aperture 55. For the cylindrical battery chamber 50 shown in FIGS. 2-4, the aperture-facing portion of the battery chamber 50 may be modified to convert the curved surface to a generally planar surface that is approximately parallel to the outward-facing surface 34 of the base layer 20. Accordingly, the aperture 55 may be configured to accommodate or engage with a head band, a goggle strap, or an eye glass temple to hold and maintain the position of the pulse-ox sensor 15 over the temporal region 60, and more specifically the temporal artery 65 (see FIGS. 5A and 5B). The temporal artery 65 is the smaller of two terminal branches (the other is the maxillary artery) that bifurcate superiorly from the external carotid artery 70 (see FIG. 5A).

Base Layer

The base layer 20, which includes the pulse-ox sensor 15 on the subject-facing surface 25, helps to secure the assembly 10 flush to the subjects' temporal region and prevents the assembly 10 from rotating or being displaced during exercise (e.g., swimming) activities. In accordance with an embodiment, the base layer 20 is configured with a large surface area flare design, relative to the surface area of the pulse-ox sensor 15. For example, a typical pulse-ox sensor 15 may have a surface area that is about 0.3 $cm^2$ to about 0.5 $cm^2$, and the base layer 20 may have a subject-facing surface area that is about 5×, about 6×, about 7×, about 8×, about 9×, about 10×, or more.

Additionally, the base layer 20 is configured to conform to a temporal region 60 of the subject's head. For example, the base layer 20 may be generally isosceles trapezoidal or "butterfly" in shape The location of the pulse-ox sensor 15 within the two-dimensional area of the subject-facing surface 25 of the base layer 20 need not be fixed to one specific area. However, placement of the pulse-ox sensor 15 centrally within the relatively larger surface area of the base layer 20 may require more adaptation to accommodate the ear tissue of the subject. While not shown, a blunted protuberance (e.g., an ear bud) may be projected from the subject-facing surface to facilitate indexing the pulse-ox sensor 15 over the temporal artery 65. In conjunction with the foregoing, the ear bud may also provide a conduit for transmitting an audible signal from the processor to the subject.

The base layer 20 and other components that contact the subject's tissue (i.e., skin and/or hair) may be made of any suitable material, such as biocompatible materials. Flexible polymeric materials, such as polyethylene, polypropylene, fluoropolymers (e.g. polytetrafluoroethylene), polyurethane, or other similarly water resistant or waterproof materials, may be suitable for use. While latex materials are not specifically excluded, the use of latex may be avoided to prevent adverse reactions induced by latex allergies.

Mounting Assembly

The aperture 55 may be configured to accommodate or engage with a head band, a goggle strap, or an eye glass temple to hold and maintain the position of the pulse-ox sensor 15 over the temporal region 60. In addition to embodiments shown in FIGS. 2-4, where the aperture-facing portion of the battery chamber 50 is shown modified to convert the curved surface to a generally planar surface that is approximately parallel to the base layer 20, other configurations or devices may be use in the mounting assembly 56. In an alternative embodiment (not shown), a clip or loop may be fixed to the outer-facing surface of the battery chamber 50. In yet another embodiment (not shown), one or more clips or loops may be fixed to the outer-facing surface 34 of the base layer 20 that are laterally disposed from the battery chamber 50. In any of the foregoing alternative embodiments, the clip(s) or loop(s) may be configured to accommodate or engage with a head band, a goggle strap, or an eye glass temple to hold and maintain the position of the pulse-ox sensor 15 over the temporal region 60, and more specifically the temporal artery 65 (see FIGS. 5A and 5B). It should be further appreciated that other structures or materials may be used to connect the assembly 10 to a head band, a goggle strap, or an eye glass temple, such as hook and loop fasteners, snaps, clasps, stitching, or the like. In other words, the assembly 10 may be directly or indirectly connected to the head band, the goggle strap, or the eye glass temple.

As shown in FIGS. 6 and 7, in accordance with another embodiment, the mounting assembly 56 may further include a set of goggles 75 and a goggle strap 80. The goggle strap 80 passes through the aperture 55 formed between the battery chamber 50 and the base layer 20. Once the subject dons the combined pulse-ox sensor assembly 10, goggles 75, and goggle strap 80, the assembly 10 may be repositioned (as indicated by the bi-directional arrow 85) to place the pulse-ox sensor 15 over the temporal artery 65. Due to the frictional force between the goggle strap 80 and internal walls of the aperture 55, as well as the stability provided to the assembly 10 by the relatively large surface area of the subject-facing surface 25, the assembly 10 resists displacement during vigorous exercise, such as swimming.

Additional Components

Pressure Sensor

The pulse-ox sensor assembly 10 may further include a pressure sensor (not shown), which is also in communication with the processor. In aqueous environments, the pressure sensor may provide an output signal to the processor indicating whether the subject's head is underwater, and optionally a depth of water above the subject's head. Accordingly, the processor may further include control logic configured to receive the output signal from the pressure sensor, determine a position of the subject's head in relation to a water surface, and generate a second output signal for the indicator device that is based on the position of the subject's head in relation to a water surface. For example, different colored lights in the LED array 40 of the indicator device 35 may be used to identify whether the subject's head is submerged. Additionally, the output of LED array 40 may be modulated to differentiate when the subject's head is above or below the water surface. Moreover the pressure sensor may be used to toggle predefined/customized power saving modes. For example, the LED array 40 and/or the pulse-ox sensor 15 may only be operational and powered once the subject is below the water surface.

In non-aqueous settings, the pressure sensor may be used as a component of an altimeter to provide information regarding absolute or changes in elevation. Additionally, global positioning system (GPS) receiver may also provide information about its location and elevation above sea level.

In accordance with an embodiment of the present invention, one purpose of the assembly 10 is to provide monitoring and assessing the physical state of active personnel. The assembly 10 described herein enables standoff monitoring of a subject's vital signs (e.g., SPO2 and HR) and provides visual alerts to observers monitoring the subject when vitals deteriorate to a predetermined threshold point prior to the need for medical intervention. For example, the assembly 10 enables determining if the subject's heart beat rate is greater than the predetermined threshold heart beat rate, determining if the subject's blood oxygen saturation level is less than the predetermined threshold blood oxygen saturation level, or both.

In aqueous environments, the pulse-ox sensor assembly 10 is a waterproof device that monitors an subject's key physiological vitals, (e.g., HR and SPO2 levels), and emits a visual notification, (e.g., a continuous light, a flashing light, illuminating different colors, etc.), when one or more vital signs reach predefined thresholds to alert observers of a warning state that the subject may be experiencing. The assembly 10 can provide an earlier positive identification when the monitored subject needs assistance, when a subject needs requires additional recovery time from exercise, and enables standoff monitoring. Advantageously, notifications to standoff observers are passively invoked requiring no interaction from the subject swimmer to initiate.

Accordingly, another embodiment of the present inventions is a method for monitoring and assessing a physical state of a subject is provided. The method includes positioning the pulse-ox sensor assembly 10 over the temporal region of the subject's head, wherein the pulse-ox sensor 15 is positioned over a portion of the temporal artery; obtaining the subject's heart beat rate, blood oxygen saturation level, or both; comparing the subject's heart beat rate to a predetermined threshold heart beat rate, and/or comparing the subject's blood oxygen saturation level to a predetermined threshold blood oxygen saturation level; and transmitting a signal to the indicator device 35 of the assembly 10 that indicates if the predetermined threshold heart beat rate and/or the predetermined threshold blood oxygen saturation level have been crossed. As noted above, the method and the assembly 10 described herein enables standoff monitoring of a subject's vital signs (e.g., SPO2 and HR) and provides visual alerts to observers monitoring the subject when vitals deteriorate to a predetermined threshold point prior to the need for medical intervention. Alternatively, audible alarms, vibrational devices, and/or radiation transmitters may also provide notification of a warning state to the monitored subject. Advantageously, notifications to standoff observers are passively invoked requiring no interaction from the monitored subject to initiate.

As used herein and in the appended claims, the singular forms "a", "an" and "the" include plural reference unless the context clearly dictates otherwise. As well, the terms "a" (or "an"), "one or more" and "at least one" can be used interchangeably herein. It is also to be noted that the terms "comprising", "including", "characterized by" and "having" can be used interchangeably.

It will be understood that when an element is described as being "connected" or "coupled" to or with another element, it can be directly connected or coupled to the other element or, instead, one or more intervening elements may be present. In contrast, when an element is described as being "directly connected" or "directly coupled" to another element, there are no intervening elements present. When an element is described as being "indirectly connected" or "indirectly coupled" to another element, there is at least one intervening element.

While the present invention has been illustrated by the description of one or more embodiments thereof, and while the embodiments have been described in considerable detail, they are not intended to restrict or in any way limit the scope of the appended claim to such detail. Additional advantages and modification will be readily apparent to those skilled in the art. The invention in its broader aspects is therefore not limited to the specific details, representative apparatus and methods and illustrative examples shown and described. Accordingly, departures may be made from such details without departing from the scope or the spirit of the general inventive concept exemplified herein.

What is claimed is:

1. A waterproof pulse oximeter sensor assembly configured to monitor vitals of a swimmer, the waterproof pulse oximeter sensor assembly comprising:
    a waterproof housing configured to be positioned proximate to a temporal artery of the swimmer;
    a pulse oximeter sensor operably coupled to the waterproof housing and configured to evaluate conditions in the temporal artery of the swimmer and to generate a pulse-ox signal in response thereto;
    a pressure sensor operably coupled to the processor and configured to detect pressure associated with a depth of water, the pressure sensor being further configured to provide a pressure sensor output signal to the processor in response to the detected pressure; and
    a processor in the waterproof housing and operably coupled to the pulse oximeter sensor, wherein the processor includes control logic configured to:
        receive the pulse-ox signal from the pulse oximeter sensor and the pressure sensor output signal from the pressure sensor,
        determine a heartbeat rate, a blood oxygen saturation level, or both from the pulse-ox signal,
        determine an underwater depth in relation to the detected pressure,
        generate an output signal that is based on the determined heartbeat rate, blood oxygen saturation level, the underwater depth, or a combination thereof, and transmit the output signal to an indicator.

2. The pulse oximeter sensor assembly of claim 1, wherein the pulse oximeter sensor comprises at least one light emitting diode and at least one photodetector.

3. The pulse oximeter sensor assembly of claim 1, further comprising:
    a network interface in the waterproof housing configured to communicate data from the processor by a protocol selected from USB, Wi-Fi, Bluetooth, IrDA, radio frequency, IEEE 802.11, IEEE 802.15, Zigbee, Free Space Optical, or combinations thereof.

4. The pulse oximeter sensor assembly of claim 1, further comprising:
    a mounting assembly operably coupled to the waterproof housing configured to receive a head band, a goggle strap, or an eye glass temple so as to secure the pulse oximeter sensor assembly to the swimmer.

5. The waterproof pulse oximeter sensor assembly of claim 1, further comprising:
    an indicator operably coupled to the waterproof housing and configured to receive the output signal from the processor and, in response to the output signal is configured to transmit a visual signal, an audible signal, a sensory signal, or a combination thereof.

6. The waterproof pulse oximeter sensor assembly of claim 5, wherein the indicator is further configured to transmit the signal at a set frequency for standoff monitoring.

7. The pulse oximeter sensor assembly of claim 5, wherein the indicator comprises a light source, a noise source, a haptic device, or combinations thereof.

8. A waterproof pulse oximeter sensor assembly configured to monitor vitals of a swimmer, the waterproof pulse oximeter sensor assembly comprising:
    a waterproof housing configured to be positioned proximate to a temporal artery of the swimmer;
    a pulse oximeter sensor operably coupled to the waterproof housing and configured to evaluate conditions in the temporal artery of the swimmer and to generate a pulse-ox signal in response thereto;
    an indicator operably coupled to the waterproof housing and configured to receive the output signal from the processor and, in response to the output signal is configured to transmit a sensory signal to the swimmer;
    a pressure sensor operably coupled to the processor and configured to detect pressure associated with a depth of water, the pressure sensor being further configured to provide a pressure sensor output signal to the processor in response to the detected pressure; and a processor in the waterproof housing and operably coupled to the pulse oximeter sensor, wherein the processor includes control logic configured to:
- receive the pulse-ox signal from the pulse oximeter sensor and the pressure sensor output signal from the pressure sensor,
- determine a heartbeat rate, a blood oxygen saturation level, or both from the pulse-ox signal,
- determine an underwater depth in relation to the detected pressure,
- generate an output signal that is based on the determined heartbeat rate, blood oxygen saturation level, the underwater depth, or a combination thereof, and
- transmit the output signal to the indicator; and wherein the indicator is further configured to transmit the sensory signal at a set frequency for standoff monitoring.

9. The pulse oximeter sensor assembly of claim 8, wherein the pulse oximeter sensor comprises at least one light emitting diode and at least one photodetector.

10. The pulse oximeter sensor assembly of claim 8, further comprising:
a network interface in the waterproof housing configured to communicate data from the processor by a protocol selected from USB, Wi-Fi, Bluetooth, IrDA, radio frequency, IEEE 802.11, IEEE 802.15, Zigbee, Free Space Optical, or combinations thereof.

11. The pulse oximeter sensor assembly of claim 10, wherein the network interface comprises a radio frequency transmitter.

* * * * *